US008992439B2

(12) United States Patent
Mulvihill et al.

(10) Patent No.: US 8,992,439 B2
(45) Date of Patent: Mar. 31, 2015

(54) MEDICAL TOOL FOR REDUCED PENETRATION FORCE

(75) Inventors: Maureen L. Mulvihill, Bellefonte, PA (US); David E. Booth, Wyomissing Hills, PA (US); Brian M. Park, State College, PA (US)

(73) Assignee: Actuated Medical, Inc., Bellefonte, PA (US)

( * ) Notice: Subject to any disclaimer, the term of this patent is extended or adjusted under 35 U.S.C. 154(b) by 161 days.

(21) Appl. No.: 13/222,363

(22) Filed: Aug. 31, 2011

(65) Prior Publication Data

US 2012/0078164 A1    Mar. 29, 2012

Related U.S. Application Data

(63) Continuation of application No. 12/163,071, filed on Jun. 27, 2008, now Pat. No. 8,043,229.

(60) Provisional application No. 60/937,749, filed on Jun. 29, 2007.

(51) Int. Cl.
*A61B 10/00* (2006.01)
*A61B 17/34* (2006.01)
*A61B 10/02* (2006.01)
*A61B 17/32* (2006.01)

(52) U.S. Cl.
CPC ........... *A61B 17/3401* (2013.01); *A61B 10/025* (2013.01); *A61B 17/320068* (2013.01); *A61B 17/3415* (2013.01); *A61B 17/3476* (2013.01)
USPC ............................ 600/562; 600/573; 600/576

(58) Field of Classification Search
CPC . A61M 5/20; A61B 17/320068; A61B 10/02; A61B 10/0275; A61B 10/0096; A61B 10/007; A61B 10/0045; A61B 5/1405
USPC ..................... 604/22; 600/562, 573, 576, 581
See application file for complete search history.

(56) References Cited

U.S. PATENT DOCUMENTS 4,804,364 A * 2/1989 Dieras et al. .................... 604/22
5,011,471 A * 4/1991 Miyazaki et al. ............... 604/22

(Continued)

FOREIGN PATENT DOCUMENTS

WO    2004091693    10/2004

OTHER PUBLICATIONS

Honda, Injector Mounting Ultrasonic Vibrator Transducer. Machine Translation of JP9239031 abstract submitted in parent application. Sep. 8, 1997.*

*Primary Examiner* — Sean Dougherty
*Assistant Examiner* — Daniel Cerioni
(74) *Attorney, Agent, or Firm* — Neal P Pierotti; Metz Lewis Brodman Must O'Keefe

(57) ABSTRACT

A medical device is provided having reduced penetration force. The device includes a body having a central hollow channel and a piezoelectric transducer received within and secured to the body. The piezoelectric transducer has a hollow portion concentric with the central hollow channel. A tubular member is associated with and in communication with the piezoelectric transducer. The tubular member has at least one open end formed concentric with the central hollow channel and the hollow portion of the piezoelectric transducer, wherein the transducer is adapted for vibrating at a frequency to produce an oscillating displacement of the tubular member.

1 Claim, 17 Drawing Sheets

(56) References Cited

U.S. PATENT DOCUMENTS

| | | | |
|---|---|---|---|
| 5,836,897 A * | 11/1998 | Sakurai et al. | 601/2 |
| 5,921,999 A * | 7/1999 | Dileo | 606/166 |
| 6,402,769 B1 * | 6/2002 | Boukhny | 606/169 |
| 2008/0001500 A1 * | 1/2008 | Moriya et al. | 310/323.04 |
| 2008/0294087 A1 * | 11/2008 | Steen et al. | 604/22 |
| 2009/0069830 A1 * | 3/2009 | Mulvihill et al. | 606/171 |

* cited by examiner

MEDICAL TOOL FOR REDUCED PENETRATION FORCE

CROSS REFERENCE TO RELATED APPLICATION

This application is a continuation of U.S. Nonprovisional patent application Ser. No. 12/163,071, now U.S. Pat. No. 8,043,229 and filed on Jun. 27, 2008 which claims benefit of U.S. Provisional Patent Application No. 60/937,749, filed on Jun. 29, 2007. The subject matter of the prior applications is incorporated in its entirety by reference thereto.

BACKGROUND OF THE INVENTION

1. Field of the Invention

The present invention generally pertains to handheld medical devices, and more specifically to high-speed electrically driven lancets; epidural catheter inserters; biopsy medical instruments, such as bone biopsy medical devices; vascular entry syringes and other catheterization needles. The invention is applicable to the delivery and removal of blood, tissues, medicine, bone marrow, nutrients or other materials within the body.

2. Description of Related Art

Vascular Entry:

Short-term or permanent central venous access, such as by catheterization, is sometimes associated with procedures such as hemodialysis, chemotherapy, bone marrow transplantation, long-term antibiotic therapy and parenteral nutrition. To perforin a catheterization, an internal vein, such as the internal jugular vein, is punctured with a single-wall puncture needle attached to a syringe (i.e., a central venous catheter introducer), thereby forming a subcutaneous tunnel to the vasculature. Once the needle is in place, a guidewire-dilator is advanced into the venous system through the subcutaneous tunnel. A catheter is then inserted through the lumen of the subcutaneous tunnel and advanced into the desired position.

There are many possible complications that make vascular entry difficult. For example, a clinician must locate and support the appropriate vein palpatively with one hand while the other hand positions the syringe and introducer needle proximally. The positioning of the proximal hand on the syringe, primarily for actuation of a plunger (for introducing anesthetics, saline and medicine, or for withdrawing blood) makes it very difficult to control the needle tip at the puncture site.

Moreover, the insertion force required for penetration of the needle into the desired position may also pose a challenge. For example, due to their elasticity and size, both skin and venous tissue can vary in the force required to penetrate. Female vascularization is typically smaller, compounding the difficulty of blood vessel entry. The needle insertion process, as performed by a skilled clinician, can be impeded by rolling of veins upon even slight tangential contact by the needle.

Procedures such as subclavian vein insertion and internal jugular venipuncture are also quite risky due to the force necessary for penetration of a needle into veins and arteries. For example, because the lung apex is close to the clavical and subclavian vein, the risk of overshooting and causing accidental pneumothorax is increased. To reduce the risk of overshooting, clinicians are advised to insert the catheterization needle and then "walk" it slowly against the edge of the collar bone. Since the applied force necessary to produce enough forward momentum to pass the overlying tissues can be relatively high, the procedure must be performed carefully and slowly. Unfortunately, because of this high force, a clinician has little time to react to stop the forward momentum immediately after successful venipuncture is achieved. In some cases, by the time a clinician can react to reduce the applied forward momentum upon overshooting the needle, pneumothorax occurs and air is immediately aspirated. At this point, advanced emergency intervention by specialized and trained assistants is required.

Advances, such as that disclosed by Yang et al. (Yang, M., Zahn, J. D., "Microneedle Insertion Force Reduction Using Vibratory Actuation", Biomedical Microdevices 6:3, 177-182, 2004) rely on a reduction in microneedle insertion force by using vibratory actuation in the "kHz range". Similar to the way a mosquito uses vibratory cutting at a frequency of 200-400 Hz to pierce the skin, Yang et al. discloses a mechanical actuator to control forces on the microneedle during insertion to minimize pain. However, Yang et al. rely on lateral motion to reduce the force which has been shown to cause thermal damage in vascular tissues. Additionally, Yang et al. provides no indication of the type of actuator and configuration of a device that would provide for such motion. Meanwhile, in the work of Podder et al., ("Effects of Velocity Modulation during Surgical Needle Insertion", Proceedings of the 2005 IEEE, Engineering in Medicine and Biology $27^{th}$ Annual Conference, Shanghai, China, Sep. 1-4, 2005), it is envisioned that for precise placement of surgical needles in soft tissue, an optimal insertion speed will minimize tissue and organ deformation. Unfortunately, while the work admits that optimal insertion occurs using a combination of a constant axial insertion speed with some rotational oscillation, it also admits that oscillatory motion increases the insertion force.

Therefore, a need exists for a central venous catheter introducer having a needle which is oscillated in an axial direction in short increments and at such a frequency as to reduce the force necessary for puncturing and thereby to reduce tissue trauma and produce a higher vessel penetration success rate.

Epidural:

Epidural anesthesia is a form of regional anesthesia involving injection of drugs directly into the epidural space. To begin the procedure, a needle is inserted from the outer layer of skin, through several tissues and finally placed within the epidural space, through which a catheter is passed. Local anesthetics are injected into the epidural space causing temporary loss of sensation and pain by blocking the transmission of pain signals through nerves in or near the spinal cord. The procedure can be unpleasant to the patient because of the high force levels required to penetrate the supraspinous ligament, interspinous ligament and ligamentum flavum. Often, because of this high force for penetration and an almost instantaneous change in resistance upon passing the needle into the epidural space (i.e., high forward momentum followed by instantaneous minimization of friction), a clinician will accidentally overshoot and puncture the dura. Upon puncturing the dura, a cerebrospinal fluid will leak into the epidural space causing the patient to experience severe post dural puncture headache, lasting from two weeks to several years. Significant leakage can cause enough intracranial hypotension as to tear veins, causing a subdural hematoma, and can cause traction injuries to the cranial nerves resulting in tinnitus, hearing loss, dizziness, facial droop, or double vision.

Currently, to minimize the possibility of a dura puncture, the epidural catheter insertion process is performed very slowly and with a 16-18 gauge, specially designed needle PA2, such as the one shown in FIG. 2 called a Tuohy needle 5. The Tuohy needle 5, has a curved tip 6, which decreases the "sharpness" at the needle and, therefore, makes accidental dura puncture more difficult. The needle also comprises an opening 7 at the tip for introducing or removing fluids and catheters. Unfortunately, this curved-tip design actually increases the force a clinician must use and makes it more difficult for a clinician to stop the forward momentum upon penetration of the dural space. Additionally, the Tuohy design increases the likelihood that a clinician relies on tactile feedback during penetration. In other words, during the insertion procedure a clinician will rely on feeling a "popping" sensation—indicative of passing the needle past the dural wall—to locate the tip of the needle and quickly stop the forward momentum being applied. Still, because penetration into other tissues, such as muscle, calcified ligament, or regular ligament may produce a similar popping, a clinician may not fully perceive the correct location of the needle tip.

Several alternate technologies have been developed that attempt to minimize the dura puncture risk, while also giving the clinician indication of successful epidural placement. For example, the detection method and apparatus disclosed in Patent Application Publication No. US 2007/0142766, the contents of which are incorporated by reference, relies on a spring-loaded plunger pushing a fluid into the epidural space upon successful entry. Accordingly, the clinician is given a visual indicator (i.e., the movement of the plunger as the fluid experiences a loss of resistance at the needle opening), and would cease applying forward force. Similarly, U.S. Pat. No. 5,681,283 also relies on a visual indicator to communicate successful entry of a needle into a cavity to the clinician. Unfortunately, while a visual indicator is a positive advancement, the actual cause of the accidental dural wall puncture—that is, the high force applied by the clinician against the needle to pass through the various tissue layers—is not addressed.

Therefore, there exists a need to provide a tool that reduces the puncture force of a needle, such as a Tuohy needle, and enables a clinician to perform a more controlled entry into the epidural space, thereby reducing the possibility of an accidental dura puncture.

Biopsy:

Biopsies are procedures in which an instrument is used to remove tissue samples from within the body. The collected samples may then be analyzed for disease, or in some cases, screened for compatibility between patients for tissue transfusions. For example, in the case of a bone biopsy, it is common to remove samples of the central tissue of bones, referred to as marrow, which is surrounded and protected by the outer layer of bone called the cortex, using a specialized manually operated collection tool, such as a JAMSHIDI®, available through Cardinal Health of McGaw Park, Ill. Bone marrow examination is used in the diagnosis of a number of conditions, including leukemia, multiple myeloma, anemia and pancytopenia. Beyond simply being drawn for purposes of diagnosing, bone marrow may also be harvested and transferred either allogenically or autologously to provide hematopoietic stem cells used to restore a patient's immune system after chemotherapy treatments.

Because the marrow is surrounded by the cortex, which is considerably harder than the trabecular bone layer and marrow, a clinician must exert a high force to introduce a biopsy instrument to penetrate the cortex. Several damaging effects can happen when high force is used to puncture through hard bone. Still, several conventional tools exist for the purpose of collecting samples of bone marrow. Typically, the tools are quite simple, such as the one shown in Prior Art FIG. 1, comprising a handle portion (not shown), and a hollow cannula 1 surrounding a stylet 2 attached to the handle portion such as that disclosed in U.S. Pat. No. 6,443,910 (Krueger et al.), which is hereby incorporated by reference. In other references, such as U.S. Pat. No. 5,885,226 (Rubinstein et al.), the contents of which are incorporated by reference, the stylet is referred to as an "inner trocar" or simply, an "introducer".

To penetrate through hard tissues, such as bone, a clinician holds a manual biopsy tool PA1 such as that shown in Prior Art FIG. 1 at the handle (not shown) and pushes the cannula 1 and stylet 2 through the bone, finally reaching the marrow. To reduce the exertion force necessary by a clinician on the device to achieve penetration of the cannula and stylet through bone, the distal tip 3 of the inner stylet or trocar is sharpened and has an angled, chisel-like face 4 which reduces the surface area. Additionally, a distal end 1' of the hollow cannula may be serrated and sharpened to aid in penetration and severing of tissues for sample collection (i.e., coring). While some reduction in force is attained using these kinds of handheld biopsy devices, clinicians find themselves not simply pushing with a longitudinal force, but also with twisting motion for successful penetration and sample collection. This twisting motion causes the tool tip to scrape and grind with the sharp tip during penetration causing fragments of the bone to break away in shards and small pieces. Unfortunately, because the tool is limited in this simple handheld design, the method to use the tool is also limited because the twisting and constant longitudinal force may result in a bone fracture, or a wound site that is not optimally formed for fast and efficient healing. Additionally, because the size of the biopsy sample is important, design changes such as larger cannula have been offered. Unfortunately, when a larger cannula is used, the result is a higher force necessary to penetrate the bone. Ultimately the larger size results in extreme pain and trauma for the patient despite local anesthesia, as disclosed in United States Patent Application Publication No. 2008/0139961 (Slama et al.). In U.S. Pat. No. 6,273,861 (Bates et al.), which is hereby incorporated by reference, it is disclosed that manual biopsy devices are hindered because the operating clinician must have a great deal of control and strength to advance the stylet through the hard cortex bone material. As a result, it takes a great deal of force to penetrate through it. Therefore, the cannula is advanced relatively slowly resulting in poor cutting action and surrounding tissue collapse.

Several advances that introduce automatic triggering mechanisms capable of increasing the speed at which the sharp tip of a device pierces through tissue have been attempted to reduce the pain experienced by patients during biopsy procedures. By automating the function of introducing the sharp tip of the devices into a patient, these devices attempt to replace the large force that a clinician must automatically apply on the tool with a quick moving, sharp tip traveling through tissue, thereby reducing pain for the patient. According to the '861 patent, these rapid fire "gun" type biopsy tools reduce the dexterity and motor coordination necessary and produce a quick, clean cut. For example, advances that allow biopsy devices to operate in a controlled "firing" manner in which the tissue is penetrated by the sampling needle at a very high velocity are disclosed in U.S. Pat. No. 7,018,343 (Plishka). Additionally, United States Patent Application Publication No. 2008/0103413 (Cicenas et al.) discloses a pneumatic, mechanically driven apparatus which is used to advance a hollow cutter at a relatively rapid speed to a first position and then advance the cutter at a relatively slower speed, while rotating the cutter to sever the tissue. Still, according to the '861 patent, these, or "gun" type biopsy devices, are limited in that many are spring-loaded and must be manually cocked, requiring a large force. Also, the resulting "firing" of these mechanically triggered devices are known to produce a jerking motion which is a problem both to the physician and patient.

While some reduction of force may be attained by quickly firing the sharp portion of a biopsy device into a patient, they are limited by the aforementioned problems. With respect to bone biopsy devices, but applicable to other medical devices, as disclosed in U.S. Pat. No. 6,730,043 (Krueger), factors, such as balancing the ability of bone biopsy devices to cut out samples in a consistent manner without unnecessary damaging forces exerted on the sample, combined with accommodating patient comfort by reducing the need for multiple-site-sampling, has proven challenging. Therefore, a need exists to overcome the challenges not addressed by conventionally available technologies that reduces the force necessary for penetration of a sharp medical element of a medical device through tissue and also has the ability to deliver or retrieve materials subcutaneously.

Specifically, a need exists in the medical device art for an improved medical device having a sharp element that is vibrated sonically and ultrasonically, thereby reducing the force required to penetrate tissue, reduces the amount of resulting tissue damage and scarring, improving vessel access success rate, minimizes catheter wound site trauma and, most importantly, improves patient comfort.

SUMMARY OF THE INVENTION

The basis of the invention is a handheld medical device, such as a central venous catheter introducer, syringe, bone biopsy device, or epidural catheter having a sharps member such as a hollow needle, Tuohy needle, or JAMSHIDI® needle, at a distal end, for use in procedures, such as vascular entry and catheterization, epidural catheterization, or bone biopsy, wherein the medical device comprises at least one driving actuator, such as a piezoelectric transducer attached to the sharps member, and wherein the piezoelectric transducer oscillates the sharps member, causing it to resonate at small displacements and high frequencies, thereby reducing the force required to penetrate through tissues.

Transducer technologies that rely on conventional, single or stacked piezoelectric ceramic assemblies for actuation are hindered by the maximum strain limit of the piezoelectric materials themselves. Because the maximum strain limit of conventional piezoelectric ceramics is about 0.1% for polycrystalline piezoelectric materials, such as ceramic lead zirconate titanate (PZT) and 0.5% for single crystal piezoelectric materials, it would require a large stack of cells to approach useful displacement or actuation of, for example, a handheld medical device usable for processes penetrating through tissues. However, using a large stack of cells to actuate components of a handpiece would also require that the tool size be increased beyond usable biometric design for handheld instruments.

Flextensional transducer assembly designs have been developed which provide amplification in piezoelectric material stack strain displacement. The flextensional designs comprise a piezoelectric material transducer driving cell disposed within a frame, platen, endcaps or housing. The geometry of the frame, platten, endcaps or housing provides amplification of the axial or longitudinal motions of the driver cell to obtain a larger displacement of the flextensional assembly in a particular direction. Essentially, the flextensional transducer assembly more efficiently converts strain in one direction into movement (or force) in a second direction. Flextensional transducers may take on several embodiments. For example, in one embodiment, flextensional transducers are of the cymbal type, as described in U.S. Pat. No. 5,729,077 (Newnham), which is hereby incorporated by reference. In another embodiment, flextensional transducers are of the amplified piezoelectric actuator ("APA") type as described in U.S. Pat. No. 6,465,936 (Knowles), which is hereby incorporated by reference. In yet another embodiment, the transducer is a Langevin or bolted dumbbell-type transducer, similar to, but not limited to that which is disclosed in United States Patent Application Publication No. 2007/0063618 A1 (Bromfield), which is hereby incorporated by reference.

In a preferred embodiment, the present invention comprises a handheld device including a body, a flextensional transducer disposed within said body and a penetrating or "sharps" member attached to one face of the flextensional transducer. The transducer may have an internal bore running from a distal end to a proximal end. The sharps member is at least a hollow tubular structure having a sharpened distal end. The hollow central portion of the sharps member is concentric to the internal bore of the transducer, together forming a continuous hollow cavity from a distal end of the transducer body to a proximal end of the sharps member. For example, the flextensional transducer assembly may utilize flextensional cymbal transducer technology or amplified piezoelectric actuator (APA) transducer technology. The flextensional transducer assembly provides for improved amplification and improved performance, which are above that of a conventional handheld device. For example, the amplification may be improved by up to about 50-fold. Additionally, the flextensional transducer assembly enables handpiece configurations to have a more simplified design and a smaller format.

One embodiment of the present invention is a resonance driven vascular entry needle to reduce insertion force of a syringe and to reduce rolling of vasculature.

An alternative embodiment of the present invention is a reduction of force epidural needle that enables the clinician a more controlled entry into the epidural space, eliminating the accidental puncturing of the dural sheath. In this embodiment, a transducer, for example, a Langevin transducer, has a hollow sharps member, for example a hollow needle, attached to a distal portion of the actuator. The Langevin transducer is open at opposite ends. These openings include a hollow portion extending continuously from the distal end of the transducer to a proximal end of the transducer. The distal opening coincides with the hollow sharps member. A plunger, having a handle, a shaft and a seal is also attached to the transducer at an opposite end of the sharps member. The plunger's shaft is slidably disposed within the continuous, hollowed inner portion of the transducer. The seal is attached to a distal portion of the plunger's shaft and separates a distal volume of the hollowed inner portion of the transducer from a proximal volume of the hollowed inner portion. Because the plunger's shaft is slidably disposed, the plunger is also slidably disposed and, in response to a motion of the shaft in a distal direction, reduces the distal volume of the hollowed inner portion and increases the proximal volume. Conversely, in response to a motion of the shaft in a proximal direction, the seal also moves in a proximal direction, thereby reducing the proximal volume of the hollowed portion and increasing the distal volume. The motion of the plunger's shaft, and, effectively, the plunger's seal, is actuated by an external force acting on the plunger's handle. When electrically activated, the transducer transfers compression and expansion of the piezoelectric ceramic portion to a hollow and sharp tip of the hollow needle.

Another embodiment of the invention provides a bone marrow biopsy device having an outer casing, a transducer, for example, a Langevin transducer, including a first body portion and a second body portion of the transducer, with piezoelectric ceramic discs formed between the first and second body portions, wherein the transducer is disposed at least partially within the casing. The invention further includes a handle, an outer cannula, such as a needle, having an open distal end and an open proximal end with the cannula positioned at a distal portion of the transducer. In one aspect of the present embodiment, the invention further comprises a stylet having a sharp distal tip attached to the handle at a portion opposite the distal tip, wherein the stylet is slidably disposed through a center cavity of the body and cannula. The transducer is formed with a distal opening formed at a distal end of the transducer, and a proximal opening formed at a proximal end of the transducer with a centralized hollow bore extending from the distal opening to the proximal opening, thereby defining a hollow channel.

More precisely, the outer cannula is a hollow tube fixedly attached at the distal end of the transducer such that the open proximal end of the cannula coincides with the distal opening of the transducer distal end. The stylet is slidably and centrally disposed within the transducer from the proximal end through the hollow channel and through the distal end. The stylet is also of predetermined length such that it is slidably and centrally located through the outer cannula, with the distal tip of the stylet protruding past the open distal end of the cannula.

According to an alternative embodiment, the transducer may be formed with a distal opening formed at the distal end of the transducer, a side port on a horn side of the transducer, and a centralized hollow bore extending from the distal opening to and in communication with the side port.

The present invention relates generally to a resonance driven, handheld device for penetration through various tissues within a body for the delivery or removal of bodily fluids, tissues, nutrients, medicines, therapies, or the like. Specifically, the present invention is a handpiece including a body, at least one piezoelectric transducer driver disposed within the body, and a sharps member for tissue penetration, such as a syringe, epidural needle or biopsy needle located at a distal portion of the handheld device.

In one embodiment, the sharp tubular member is a syringe.

In another embodiment, the sharp tubular member is a Tuohy needle.

In yet another embodiment, the sharp tubular member is a trocar and stylet assembly, such as a JAMSHIDI® needle.

These and other features of this invention are described in, or are apparent from, the following detailed description of various exemplary embodiments of this invention.

BRIEF DESCRIPTION OF THE DRAWINGS

Exemplary embodiments of this invention will be described with reference to the accompanying figures.

REFERENCE LABELS

Figure 1:
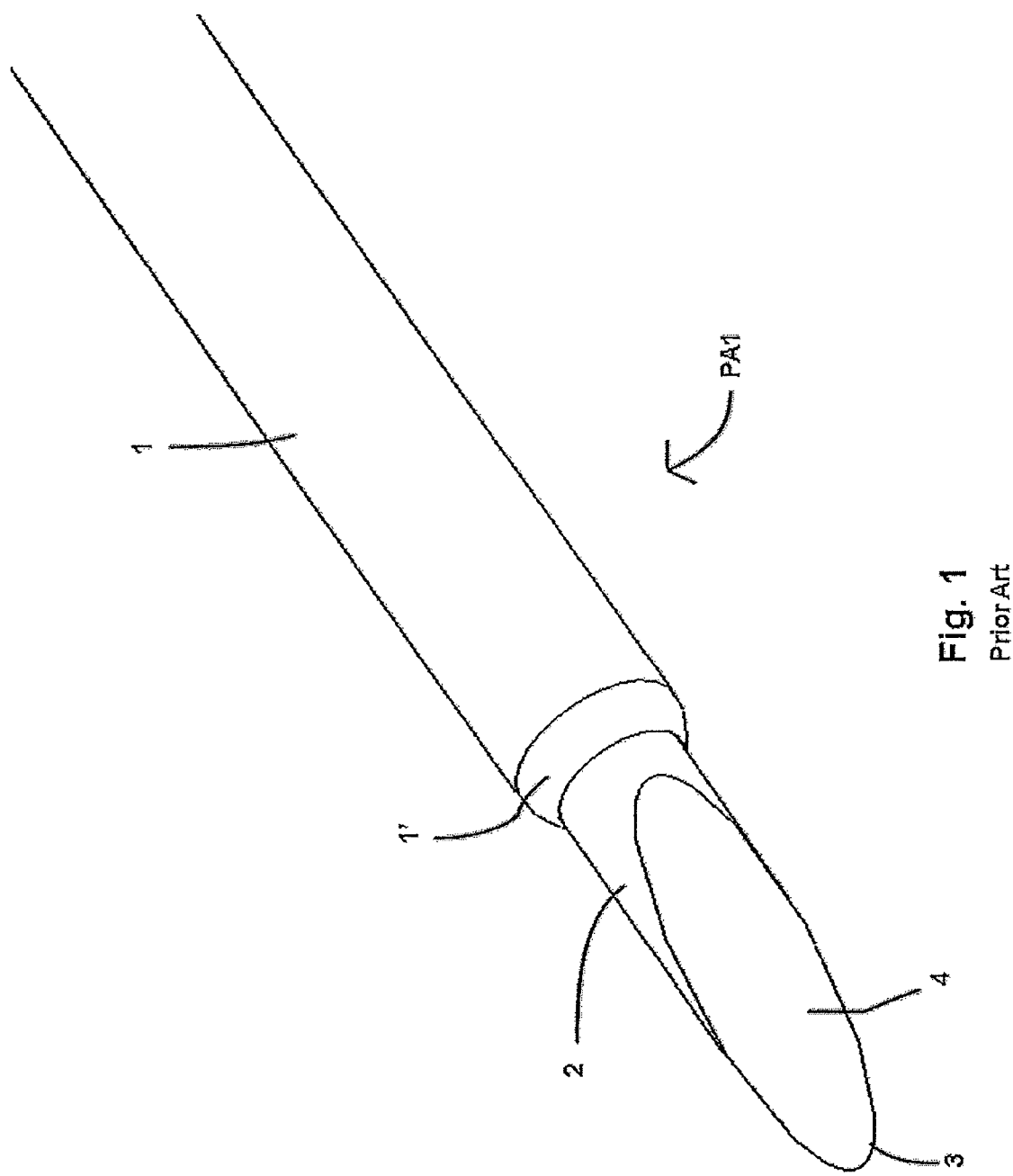
FIG. 1 is a sketch of a Prior Art biopsy needle.
Figure 2:
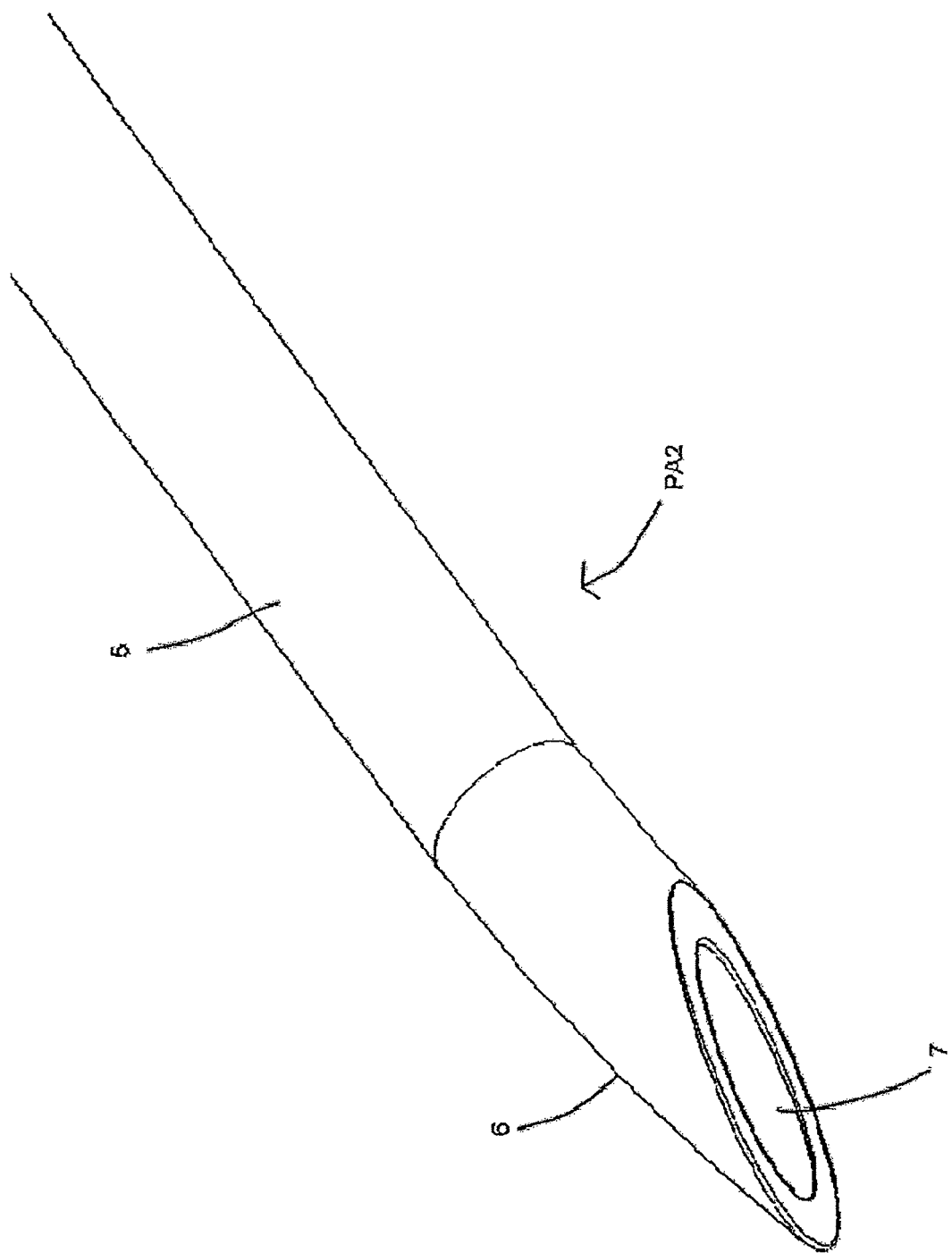
FIG. 2 is a sketch of a Prior Art epidural needle.

A Static needle force curve
B Vibrating needle force curve
PA1 Conventional biopsy needle
PA2 Conventional epidural needle
1 Cannula
1' Cannula distal end
2 Stylet
3 Distal tip
4 Stylet tip angled face
5 Tuohy needle
6 Tuohy curved tip
7 Tip opening
100 Langevin transducer
110 Horn
111 Support wings
112 Rear mass
114 Piezoelectric rings
116 Bolt
118 Handle
120 Seal
121 Distal face
122 Distal opening
124 Proximal opening
126 Bore
10 Sharps member
128 Attachment fitting
129 Catheter
130 Hollow needle
130a Proximal end of hollow needle
12 Plunger
132 Plunger handle
134 Plunger shaft
134a Proximal end of plunger shaft
134b Distal end of plunger shaft
136 Plunger seal
200 Sharps Introducer
201 Supported Introducer
202 Catheterization Introducer
14 Inner Stylet
142 Inner stylet handle
144 Inner Stylet shaft
146 Inner stylet tip
15 Outer trocar tube
148 Trocar attachment fitting 150 Outer Trocar body
152 Distal Trocar opening
154 Distal Trocar tip
300 Bone Biopsy Device
400 Advanced Bone Biopsy Device
16 APA needle
500 APA Syringe
510 APA flextensional transducer
512 Frame
512a Proximal end of frame
512b Distal end of frame
513 Needle
513a Proximal end of needle
513b Distal tip of needle
514 Piezoelectric ceramic
516 APA attachment point
518 Handle
521 Handle distal opening
524 Handle proximal opening
526 APA bore
600 Cymbal Syringe
610 Cymbal transducer
612 Distal endcap
612' Proximal endcap
616 Cymbal attachment point

BRIEF DESCRIPTION OF THE INVENTION

The preferred embodiments of the present invention are illustrated in FIGS. 3-15 with the numerals referring to like and corresponding parts. For purposes of describing relative configuration of various elements of the invention, the terms "distal", "distally", "proximal" or "proximally" are not defined so narrowly as to mean a particular rigid direction, but, rather, are used as placeholders to define relative locations which shall be defined in context with the attached drawings and reference numerals.

The effectiveness of the invention as described, for example, in the aforementioned preferred embodiments, relies on the reduction of force principle in order to optimize penetrating through tissue or materials found within the body. Essentially, when tissue is penetrated by the high speed operation of a sharps member portion of the device, such as a needle, the force required for entry is reduced. In other words, a reduction of force effect is observed when a sharps member, for example a needle, is vibrated axially during the insertion process and enough mechanical energy is present to break adhesive bonds between tissue and blade. The threshold limits of energy can be reached in the far-sonic or ultrasonic frequency ranges if the necessary amount of needle displacement is present.

To exploit the reduction of force effect, the medical device of the present invention is designed such that the sharp distal tip portion attains a short travel distance or displacement, and vibrates sinusoidally with a high penetrating frequency. Utilizing the various device configurations as described in the aforementioned embodiments, it has been determined that the sinusoidal motion of the sharp distal tip must include a displacement of between 35-100 μm, more preferably between 50-10 μm, at a frequency of between 20-50 kHz, but most preferably at 38 kHz. This motion is caused by the sharps members member being attached to an actuating transducer operated at 50-150 Vpp/mm, but most preferably at 90 Vpp/mm where Vpp is known as the peak-to-peak voltage.

Figure 3:
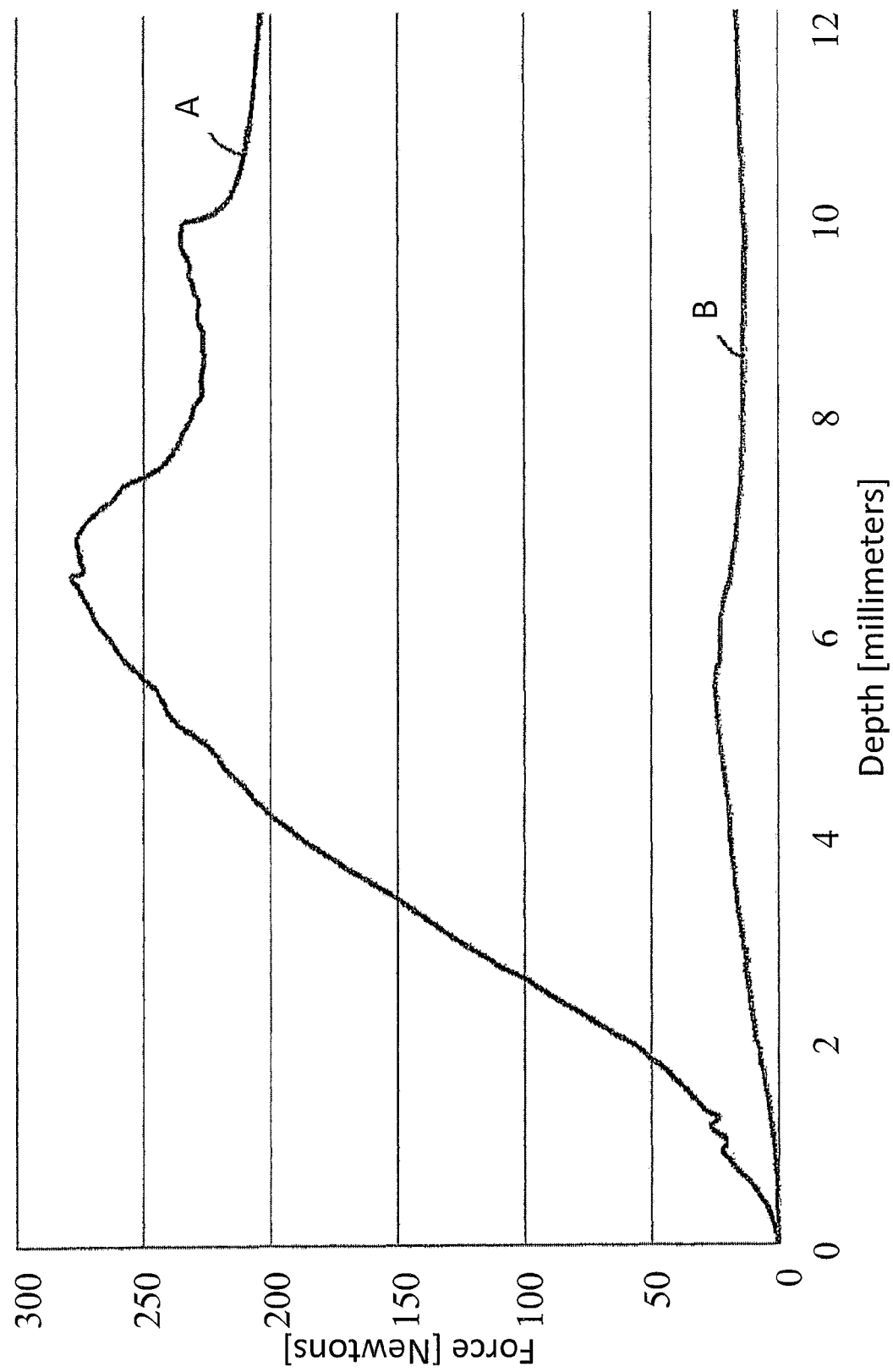
FIG. 3 is a graph illustrating the penetration force of a sharps member.

For example, FIG. 3 shows a graphical representation of the resisting force versus depth of a bone biopsy needle penetrating into hard tissue. In FIG. 3, the curve labeled A represents data for a needle in an "off" or non-vibrating condition and the curve labeled B represents data for a medical device having a needle that is vibrated at 38 kHz and a displacement of 100 μm. As apparent from FIG. 3, curve A shows that without being vibrated, the force necessary to penetrate into a material is much higher than that for a needle being oscillated, such as that represented by curve B.

Figure 4:
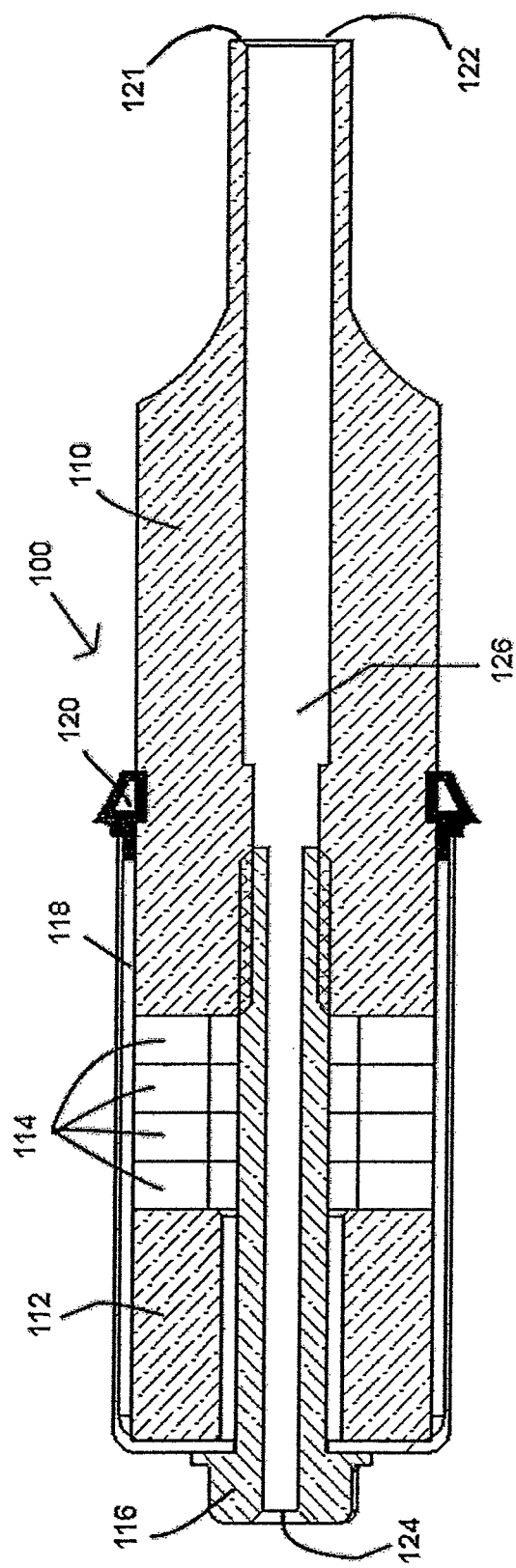
FIG. 4 is a cross section of a Langevin transducer for use as an actuator in a first embodiment of the present invention.

Referring to FIG. 4, a Langevin transducer, generally indicated as 100, piezoelectric actuator comprises a body having a central hollow channel and including a horn 110, rear mass 112 and at least one piezoelectric ceramic ring 114, but preferably comprises more than one of piezoelectric ceramic ring 114 forming a hollow portion and wherein the ceramic ring 114 are secured within the body and attached between horn 110 and rear mass 112. A hollow threaded bolt 116 is disposed within a center portion of rear mass 112, extending through a center portion of the at least one of piezoelectric ceramic ring 114 and ending within a central portion of horn 110. The bolt compresses the rear mass 112, the at least one of piezoelectric ring 114 and horn 110. The horn 110 and rear mass 112 are made of a metal such as titanium, stainless steel or, preferably, aluminum. The bolt 116 is of the same material as the horn 110 and rear mass 112. To protect a user from electric shock, at least a portion of the Langevin transducer 100, preferably at least the whole of the rear body 112, all of the at least one piezoelectric ceramic ring 114, and at least a portion of the horn 110, are disposed within a handle 118. Electrical connection is made at metallic tabs (not shown) formed between opposing faces of the at least one of piezoelectric ceramic ring 114. The handle 118 comprises a shell portion which may be a plastic or a metal and a seal 120 which may be an elastomer. Seal 120 prevents moisture from entering or exiting from the central portions of the rear mass 112, piezoelectric ceramic rings 114 and horn 110. The central portion of the rear mass 112, piezoelectric ceramic rings 114 and horn 110 coincide with the hollow portion of the bolt 116 forming a continuous bore 126 within the Langevin transducer 100, the bore 126 having a distal opening 122 at a distal face 121 and a proximal opening 124 at a face opposite to the distal face 121.

According to an alternative embodiment, a side port (not shown) may be formed at the horn 110 side of the transducer and the continuous bore 126 extends from a distal opening 122 at distal face 121 and in communication with this side port.

The functional performance of the medical device is driven by the piezoelectric elements section. Piezoelectric ceramic elements, such as each of one or more piezoelectric ceramic rings 114 are capable of precise, controlled displacement and can generate energy at a specific frequency. The piezoelectric ceramics expand when exposed to an electrical input, due to the asymmetry of the crystal structure, in a process known as the converse piezoelectric effect. Contraction is also possible with negative voltage. Piezoelectric strain is quantified through the piezoelectric coefficients $d_{33}$, $d_{31}$, and $d_{15}$, multiplied by the electric field, E, to determine the strain, x, induced in the material. Ferroelectric polycrystalline ceramics, such as barium titanate (BT) and lead zirconate titanate (PZT), exhibit piezoelectricity when electrically poled. Simple devices composed of a disk or a multilayer type directly use the strain induced in a ceramic by the applied electric field. Acoustic and ultrasonic vibrations can be generated by an alternating field tuned at the mechanical resonance frequency of a piezoelectric device. Piezoelectric components can be fabricated in a wide range of shapes and sizes. A piezoelectric component may be 2-5 mm in diameter and 3-5 mm long, possibly composed of several stacked rings, disks or plates. The exact dimensions of the piezoelectric component are performance dependent.

The piezoelectric ceramic material may be comprised of at least one of lead zirconate titanate (PZT), multilayer PZT, polyvinylidene difluoride (PVDF), multilayer PVDF, lead magnesium niobate-lead titanate (PMNPT), multilayer PMN, electrostrictive PMN-PT, ferroelectric polymers, single crystal PMN-PT (lead zinc-titanate), and single crystal PZN-PT.

Figure 5:
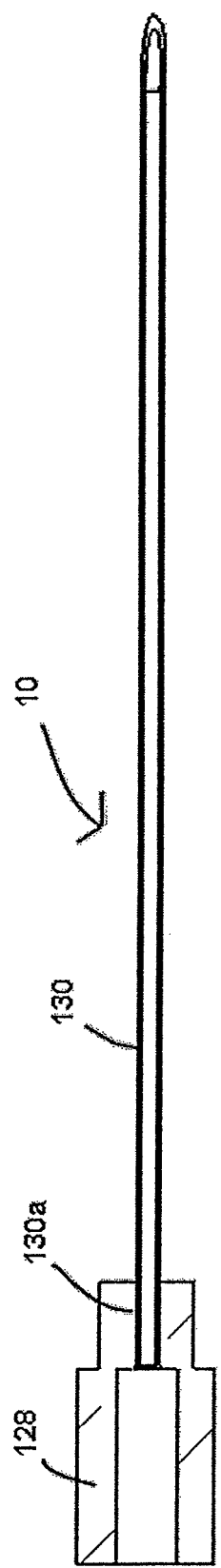
FIG. 5 is a cross section of a vascular entry needle used in a first embodiment of the invention.

Referring now to FIG. 5, a sharps member, generally indicated as 10, for use in a first embodiment of the present invention comprises an attachment fitting 128 connected to a proximal end 130a of a hollow needle 130.

Figure 6:
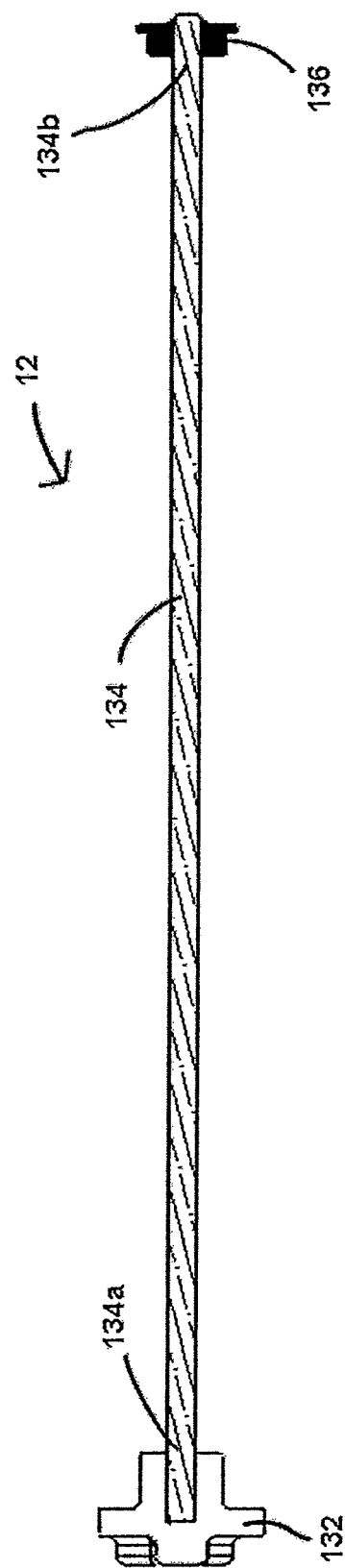
FIG. 6 is a cross section of a plunger used in a first embodiment of the invention.

Referring now to FIG. 6, a plunger, generally indicated as 12, for use in a first embodiment of the present invention comprises a plunger handle 132 attached to a proximal end 134a of a plunger shaft 134, and a plunger seal 136 attached to a distal end 134b of the plunger shaft 134.

Figure 7:
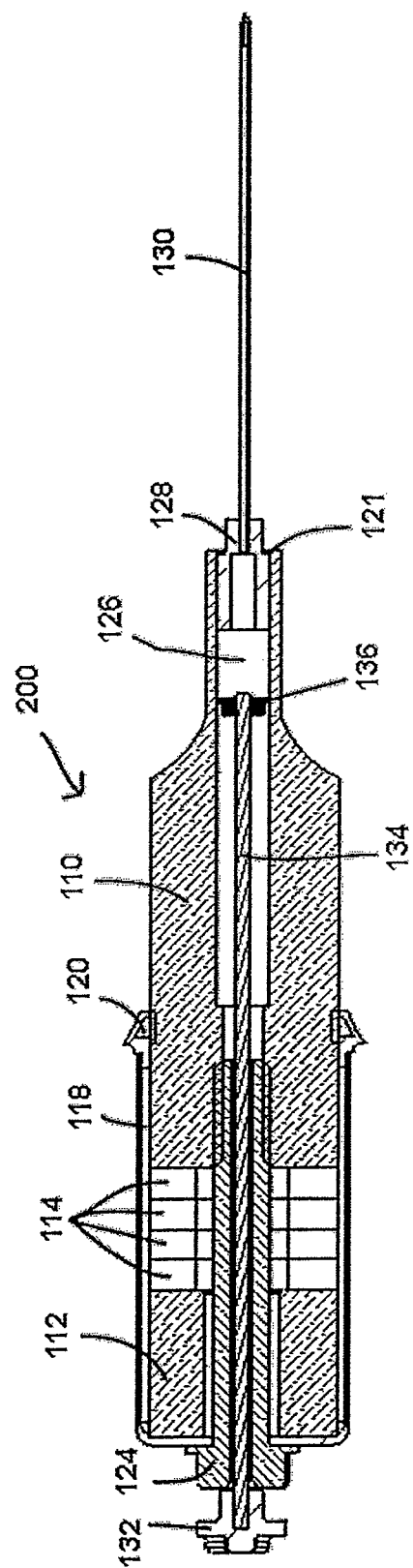
FIG. 7 is a cross section of a first embodiment of the invention.

Referring now to FIG. 7, a first embodiment of the present invention, for example a sharps introducer, generally indicated as 200, comprises a transducer, such as the Langevin transducer described in FIG. 4, with the sharps member 10 of FIG. 5 being attached at a distal face 121 of the transducer. The attachment fitting 128 is a threaded fitting, compression fitting or the like, and couples hollow needle 130 to a portion of distal face 121 such that it communicates with a distal volume of continuous bore 126. Plunger handle 132 may be threaded, clamped, compressed or the like to bolt 124 so as to immobilize plunger 12 of FIG. 6.

Returning to FIGS. 4 and 7, upon application of an external AC current at a predetermined frequency to the at least one of piezoelectric ceramic rings 114, Langevin transducer 100 reactively changes shape in a sinusoidal fashion such that the relative position of distal face 121 with respect to say, a fixed position of plunger handle 132 attached to and held in place by bolt 116, changes by a predetermined displacement. Because the AC current is a sinusoidal signal, the result of activating the piezoelectric ceramic rings 114 is a sinusoidal, back and forth motion of the distal face 121 of horn 110, and, subsequently, a back and forth motion of hollow needle 130, thereby reducing the force necessary for penetration through tissue.

Figure 8:
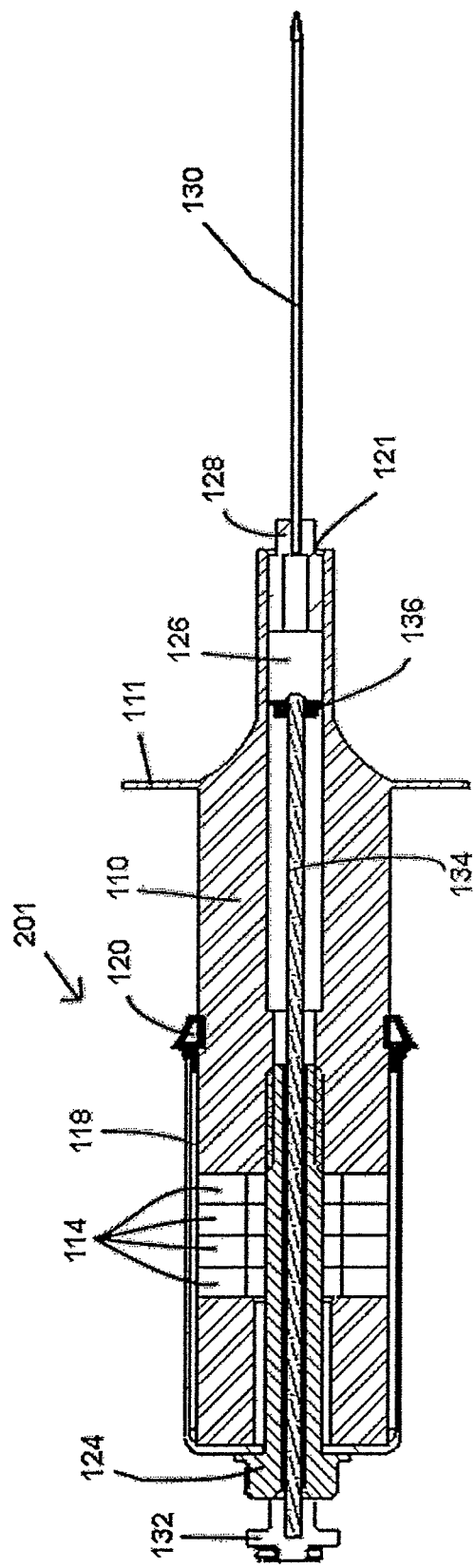
FIG. 8 is a cross section of an alternate design of the first embodiment of the invention of FIG. 7.

Referring to FIG. 8, a supported introducer, generally indicated as 201, is similar to the sharps introducer 200 of FIG. 7 additionally comprising support wings 111, existing for example as a flat portion onto which a user can grasp, and extending radially from an outer surface forming a mechanical zero-node of the horn 110.

Figure 9:
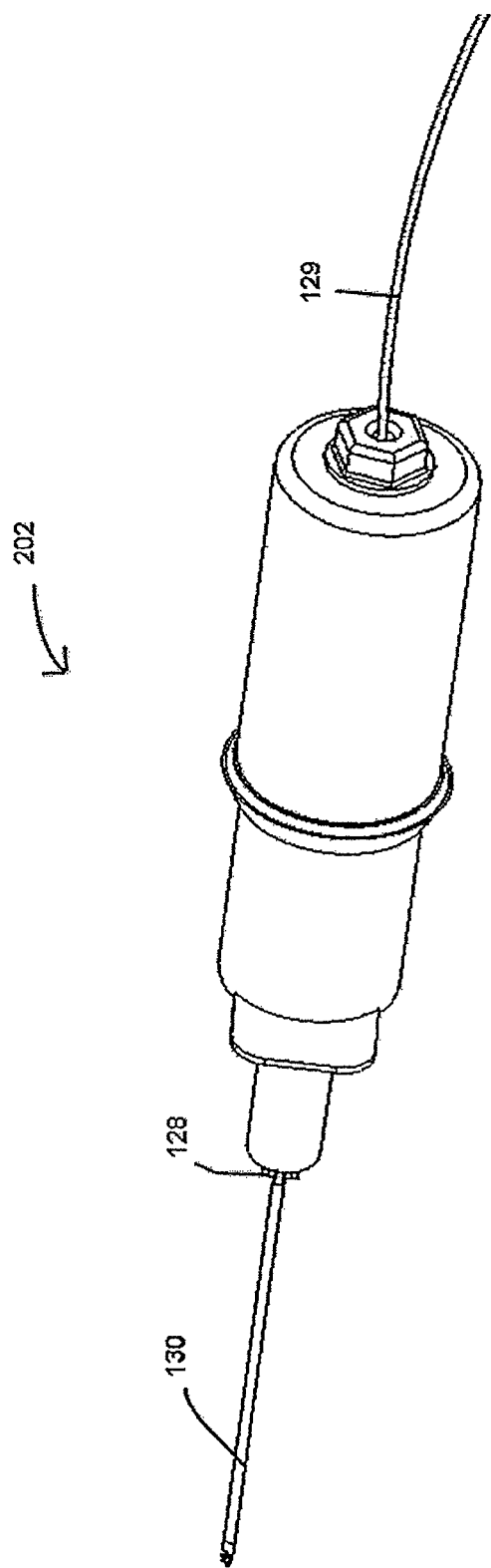
FIG. 9 is a sectional view of a second embodiment of the present invention.
Figure 10:
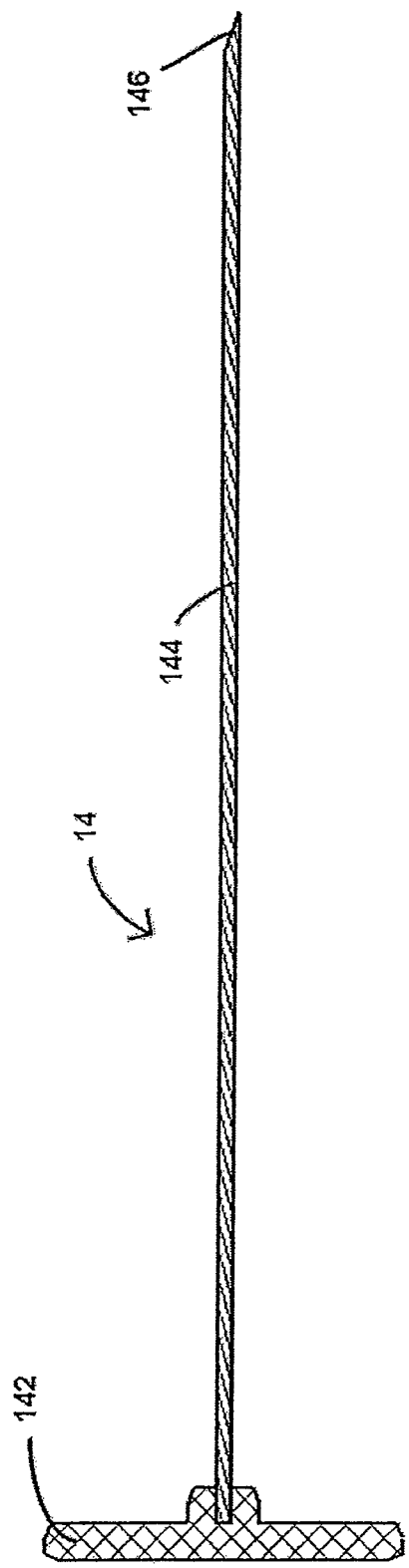
FIG. 10a is a cross section of an inner stylet for use in a third embodiment of the present invention.
FIG. 10b is a cross-section of an outer sharps member, such as a trocar, for use in a third embodiment of the present invention.
FIG. 10c is a cross-section showing the relative positioning of the inner stylet of FIG. 10a within the outer sharps member of FIG. 10b for use in a third embodiment of the present invention.
Figure 10:
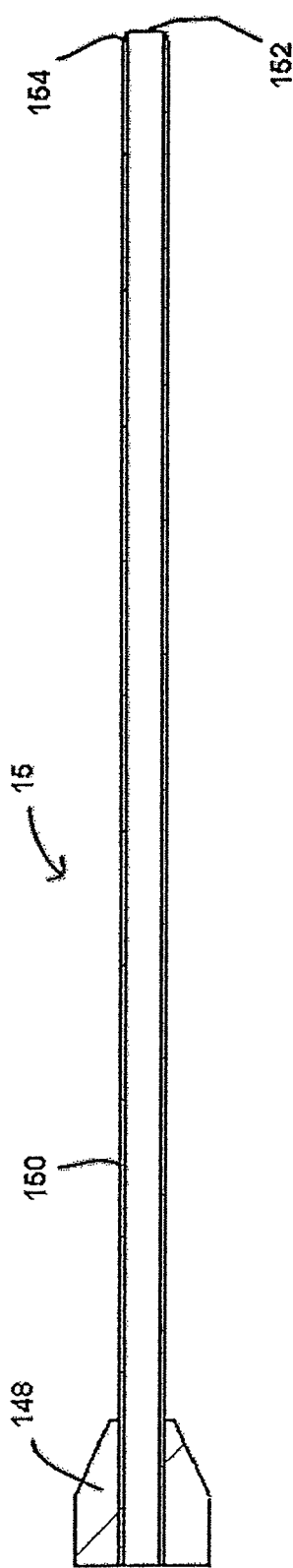
Figure 10:
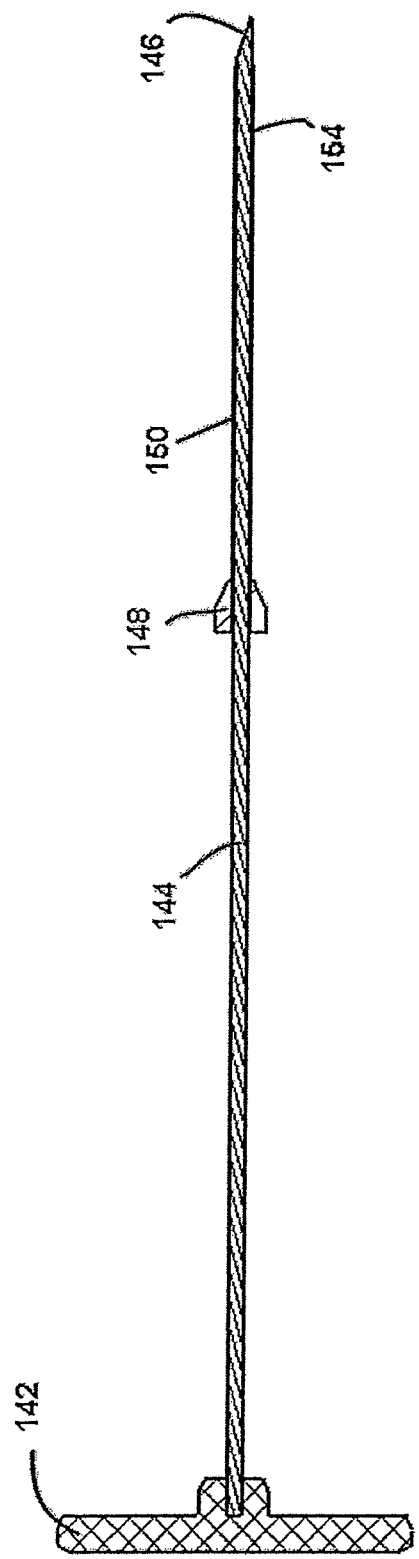

In an alternate embodiment of the present invention, the sharps introducer 201 of FIG. 8 exists as a catheterization introducer, generally indicated as 202, as shown in FIG. 9. In this embodiment, rather than a plunger being introduced from a proximal end of the device, a catheter 129 is introduced from the proximal end of the device and is received through bore 126 as shown in FIG. 4, and may be passed through hollow needle 130. Upon having been inserted into a patient, hollow needle 130 forms a subcutaneous tunnel through which catheter 129 is introduced into the body. Upon successful introduction, the transducer may be detached from hollow needle 130 by decoupling attachment fitting 128 from the horn 110.

Now referring to FIG. 10(a), an inner stylet, generally indicated as 14, comprises an inner stylet handle 142 attached to a proximal end of an inner stylet shaft 144. At a distal end of the inner stylet shaft 144, opposite to the handle 142 is a sharpened inner stylet tip 146. To support the inner stylet shaft 144, an outer trocar tube, generally indicated as 15, shown in FIG. 10(b) comprises a trocar attachment fitting 148 attached at a proximal end of an outer trocar body 150, which is a tubular structure open at opposite ends. The trocar attachment fitting 148 is hollow such that outer trocar body 150 is disposed within it. Additionally, one of the openings formed at opposite ends of the trocar body 150 is a distal trocar opening 152, the outer walls of which form distal trocar tip 154. As shown in FIG. 10(c), inner stylet shaft 144 may be slidably disposed within outer trocar body 150 with inner stylet tip 146 extending beyond distal trocar tip 154. Together, the inner stylet 14 of FIG. 10a and outer trocar tube 15 of FIG. 10b form a structure similar to a JAMSHIDI® needle.

Figure 11:
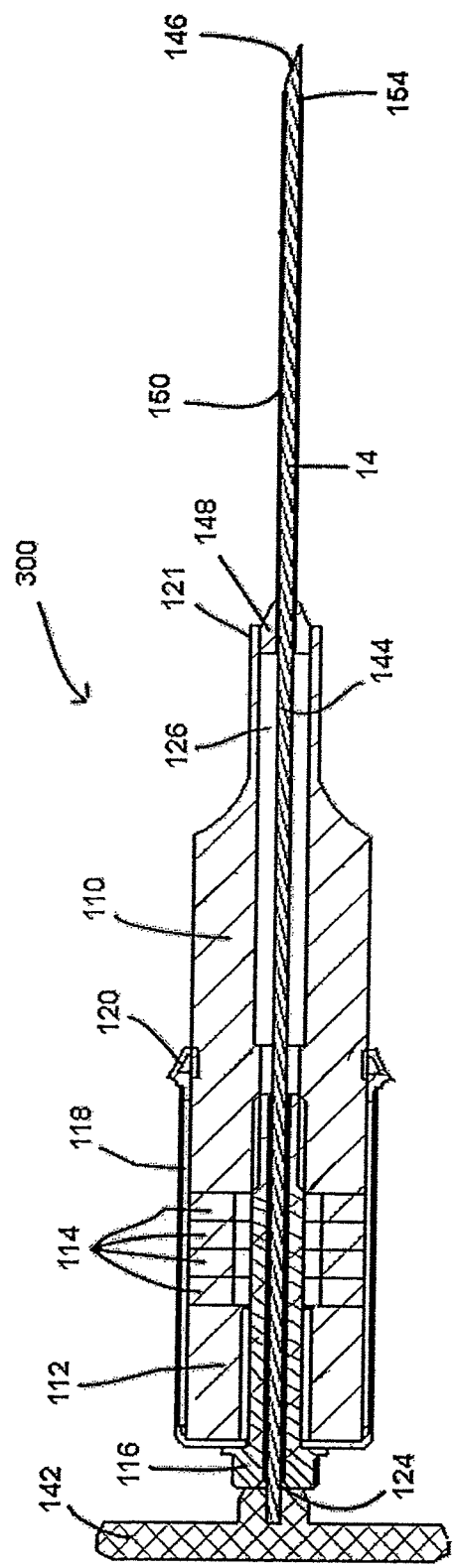
FIG. 11 is a cross section of a third embodiment of the present invention.

Referring now to FIG. 11, inner stylet 14 is slidably disposed within bore 126 of Langevin transducer 100 of FIG. 4 and outer trocar tube 15 of FIG. 10b, with outer trocar tube 15 attached to horn 110 to form a bone biopsy device, generally designated as 300. Inner stylet 14 extends in a manner such that handle 142 contacts bolt 116 when fully seated, with inner stylet shaft extending from handle 142 through proximal opening 124, through bore 126 and hollow portion of outer trocar body 150 finally terminating as inner stylet tip 146 at a location beyond distal trocar tip 154. In this embodiment, when the at least one of piezoelectric ceramic rings 114 of Langevin transducer 100 of FIG. 4 is electrically actuated at a predetermined frequency, motion in the form of compression and expansion of the rings is transferred to an anti-node location at the distal face 121 of horn 110. The motion is then transferred as actuation of outer trocar tube 15 of FIG. 10b.

Figure 12:
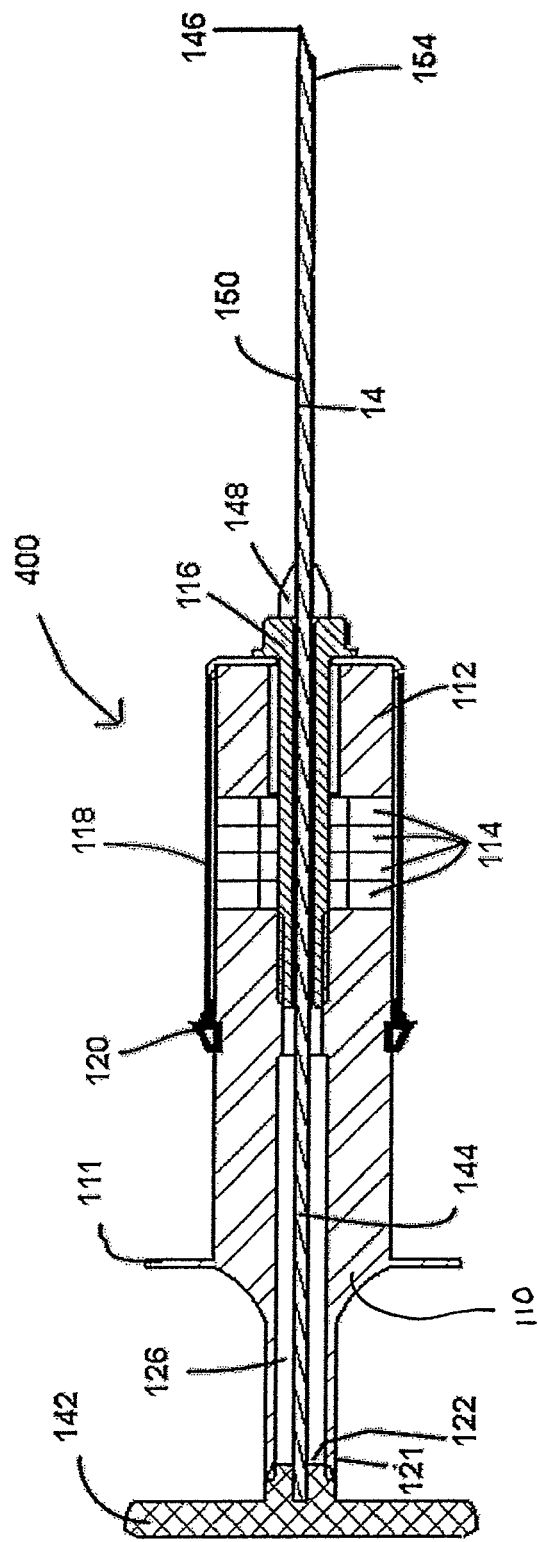
FIG. 12 is a cross section of a fourth embodiment of the present invention.

In an alternate embodiment, an advanced bone biopsy device, generally indicated as 400, shown in FIG. 12, comprises all of the elements of bone biopsy device 300 of FIG. 11, except that upon electrical activation of Langevin transducer 100 of FIG. 4 at a predetermined frequency, the motion is transferred as actuation of inner stylet 14. To perform this function, the positioning of the inner stylet shaft 14 of FIG. 10a and outer trocar tube 15 of FIG. 10b are reversed with respect to the configuration of FIG. 11. For example, in the advanced bone biopsy device 400, outer trocar tube 15 is attached to bolt 116. Additionally, inner stylet 14 extends in a manner such that handle 142 contacts distal face 121 of horn 110 when fully seated, with inner stylet shaft 144 extending from handle 142 through distal opening 122, through bore 126 and hollow portion of outer trocar body 150, finally terminating as inner stylet tip 146 at a location beyond distal trocar tip 154.

Figure 13:
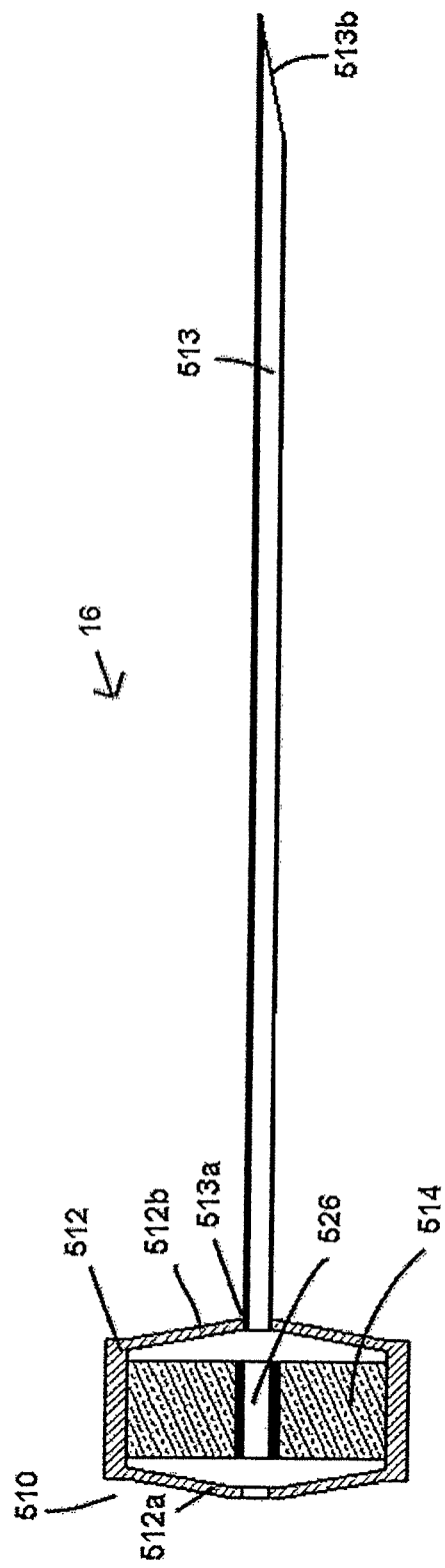
FIG. 13 is a cross section of a penetrating member attached to an amplified piezoelectric actuator for use in a fifth embodiment of the present invention.
Figure 14:
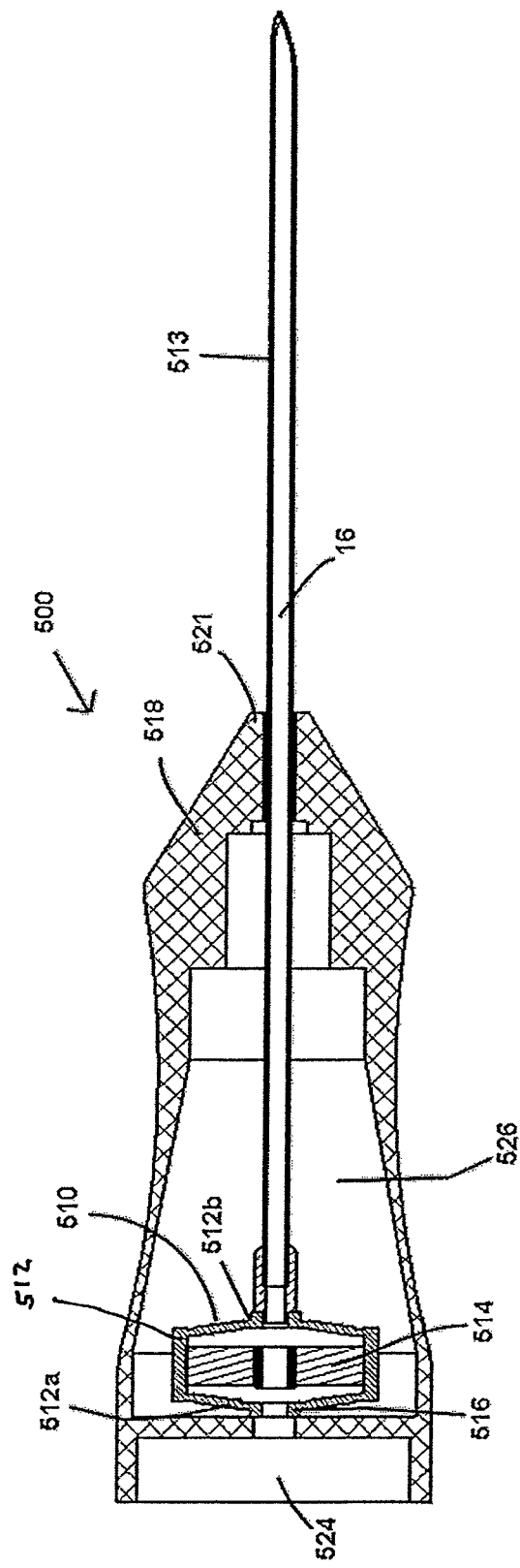
FIG. 14 is a cross section of a fifth embodiment of the present invention.

While the previous embodiments have been described with respect to a Langevin transducer 100 as the actuating mechanism, the invention is not so limited. For example, as shown in FIG. 13, a hollow tubular structure having a sharpened distal tip 513b, such as a needle 513, is attached at its proximal end 513a to an amplified piezoelectric actuator (APA) type flextensional transducer 510 forming an APA needle, generally designated as 16. The APA flextensional transducer 510 comprises a frame 512, formed of a metal such as brass or stainless steel, and a piezoelectric ceramic 514 compressed within frame 512. An APA bore 526 may extend from a distal face through piezoelectric ceramic 514 and through a proximal face 512a of frame 512. Hollow needle 513, for example a hypodermic needle, is attached to the distal face 512b of frame 512, such that the hollow portion is concentrically aligned with the APA bore 526. As shown in FIG. 14, APA needle 16 may be disposed within a handle 518 forming an APA syringe, generally designated as 500. Important to this embodiment is that a proximal face 512a of frame 512 of APA flextensional transducer 510 must be fixed as shown at 516 attachment point to an inner portion of handle 518 such that the APA bore 526, hollow needle 513, a handle proximal opening 524 and handle distal opening 521 form a continuous channel through which fluids may pass into a patient.

In operation, the piezoelectric ceramic 514 expands during the positive cycle of an AC voltage, which causes the frame's proximal and distal faces 512a, 512b formed opposite of one another to move inward toward each other. Conversely, when piezoelectric ceramic 514 compresses during the negative AC cycle, an outward displacement of the frame's proximal and distal faces 512a, 512b away from one another occurs. However, in the present embodiment, the proximal face 512a of the frame is fixedly attached to body's 518 attachment point 516 so that any movement in the piezoelectric ceramic stack will result in only a relative motion of distal face 512b and, thereby, a motion of the needle 513.

Two examples of applicable APA transducers are the non-hinged type, and the grooved or hinged type. Details of the mechanics, operation and design of an example hinged or grooved APA transducer are described in U.S. Pat. No. 6,465,936 (Knowles et al.), which is hereby incorporated by reference in its entirety. An example of a non-hinged APA transducer is the Cedrat APA50XS, sold by Cedrat Technologies, and described in the Cedrat Piezo Products Catalogue "Piezo Actuators & Electronics" (Copyright Cedrat Technologies June 2005).

Preferably, the APA transducers of the present invention are operated at frequencies in the range of 100 Hz to 20 kHz, more preferably 100 Hz to 1 kHz.

Figure 15:
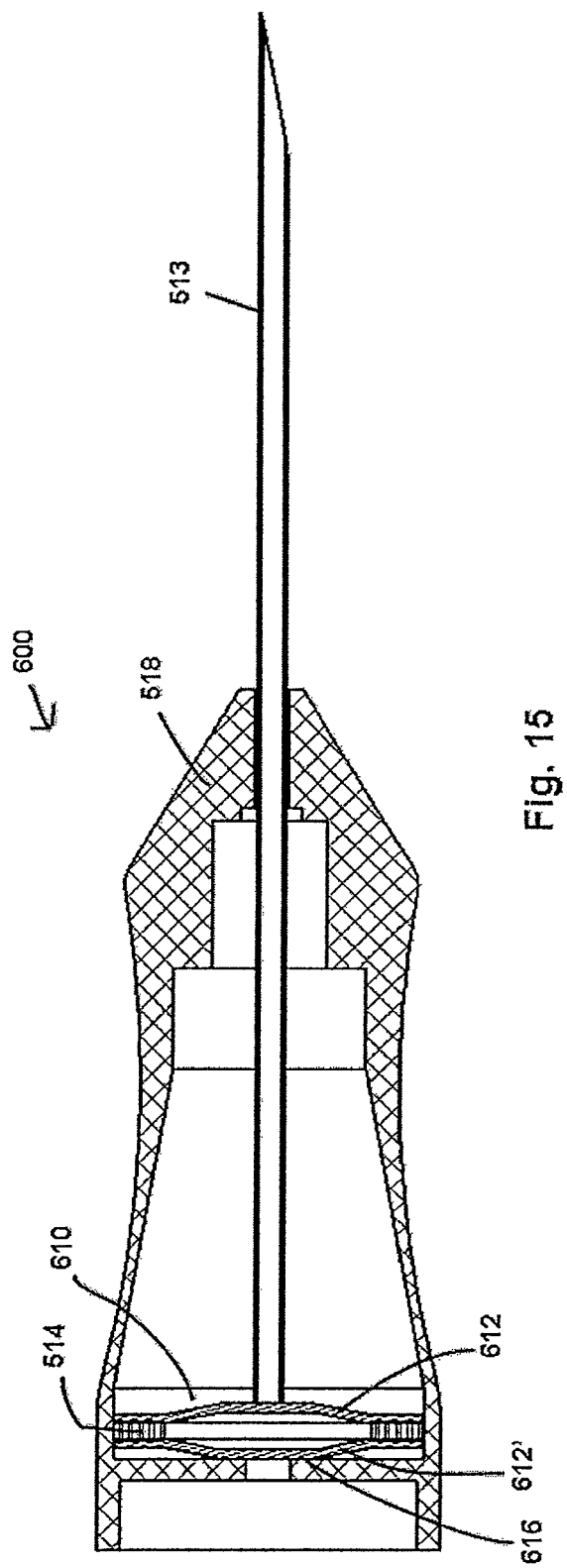
FIG. 15 is a cross section of a sixth embodiment of the present invention comprising a cymbal transducer.

Alternatively, the transducer of the present invention may be a cymbal transducer. For example, in FIG. 15, a cymbal syringe, generally indicated as 600, including a cymbal transducer 610 which comprises distal endcap 612 and proximal endcap 612' with at least a piezoelectric ceramic ring 514 formed between the endcaps. The endcaps 612 and 612' enhance the mechanical response to an electrical input, or conversely, the electrical output generated by a mechanical load. Details of the flextensional cymbal transducer technology is described by Meyer Jr., R. J., et al., "Displacement amplification of electroactive materials using the cymbal flextensional transducer", Sensors and Actuators A 87 (2001), 157-162. By way of example, a Class V flextensional cymbal transducer has a thickness of less than about 2 mm, weighs less than about 3 grams and resonates between about 1 and 100 kHz depending on geometry. With the low profile of the cymbal design, high frequency radial motions of the piezoelectric material are transformed into low frequency (about 20-50 kHz) displacement motions through the cap-covered cavity. An example of a cymbal transducer is described in U.S. Pat. No. 5,729,077 (Newnham et al.) and is hereby incorporated by reference. While the endcaps shown in the figures are round, they are not intended to be limited to only one shape or design. For example, a rectangular cymbal endcap design is disclosed in Smith N. B., et al., "Rectangular cymbal arrays for improved ultrasonic transdermal insulin delivery", J. Acoust. Soc. Am. Vol. 122, issue 4, October 2007. Cymbal transducers take advantage of the combined expansion in the piezoelectric charge coefficient $d_{33}$ (induced strain in direction 3 per unit field applied in direction 3) and contraction in the $d_{31}$ (induced strain in direction 1 per unit field applied in direction 3) of a piezoelectric material, along with the flextensional displacement of the endcaps 612 and 612', which is illustrated in FIG. 15. The design of the endcaps 612 and 612' allows both the longitudinal and transverse responses to contribute to the strain in the desired direction, creating an effective piezoelectric charge constant ($d_{eff}$) according to the formula, $d_{eff}=d_{33}+(-A*d_{31})$. Since $d_{31}$ is negative, and the amplification factor (A) can be as high as 100 as the endcaps 612 and 612' bend, the increase in displacement generated by the cymbal compared to the piezoelectric material alone is significant. The endcaps 612 and 612' can be made of a variety of materials, such as brass, steel, or KOVAR™, a nickel-cobalt ferrous alloy compatible with the thermal expansion of borosilicate glass which allows direct mechanical connections over a range of temperatures, optimized for performance and application conditions. The endcaps 612 and 612' also provide additional mechanical stability, ensuring long lifetimes for the cymbal transducers.

The cymbal transducer 610 drives the needle 513. When activated by an AC current, the cymbal transducer 610 vibrates sinusoidally with respect to the current's frequency. Because endcap 612' is fixed to an inner sidewall of body 518, when transducer 610 is activated, endcap 612 moves with respect to the body in a direction parallel to the hypothetical long axis of the medical device. Further, the displacement of needle 513 is amplified relative to the displacement originating at piezoelectric material 514 when it compresses and expands during activation due in part to the amplification caused by the design of endcaps 612 and 612'. For example, the piezoelectric material 514 alone may only displace by about 1-2 microns, but attached to the endcaps 612 and 612', the cymbal transducer 610 as a whole may generate up to about 11 kN (225 lb-f) of force and about 80 to 100 microns of displacement. This motion is further transferred through the needle 513 as an amplified longitudinal displacement of 100-300 microns. For cases requiring higher displacement, a plurality of cymbal transducers 610 can be stacked endcap-to-endcap to increase the total longitudinal displacement of the needle 513.

While the above-described embodiments of the present invention are made with respect to a handheld medical tool having a vibrating sharps member and utilizing a Langevin transducer, cymbal transducer, or APA type transducer for actuation, the present invention is not limited to these transducer assemblies. Generally, any type of motor comprising a transducer assembly, further comprising a mass coupled to a piezoelectric material, the transducer assembly having a geometry which upon actuation amplifies the motion in a direction beyond the maximum strain of the piezoelectric material, would also fall within the spirit and scope of the invention.

From the above description, it may be appreciated that the present invention provides significant benefits over conventional medical devices. The configuration of the actuating means described above, such as embodiments comprising a Langevin transducer actuator, cymbal transducer actuator, or an APA transducer actuator, accommodates the use of piezoelectric actuating members in a medical instrument by enabling the displacement of the penetrating sharps member or needle to such frequencies that cause a reduction of force needed for penetrating through tissue during procedures such as bone biopsy, epidural catheterization or vascular entry. Electrical signal control facilitated by an electrically coupled feedback system could provide the capability of high oscillation rate actuation, control over penetration depth, and low traction force for these procedures.

Now that exemplary embodiments of the present invention have been shown and described in detail, various modifications and improvements thereon will become readily apparent to those skilled in the art. While the foregoing embodiments may have dealt with the penetration through skin, bone, veins and ligaments as exemplary biological tissues, the present invention can undoubtedly ensure similar effects with other tissues which are commonly penetrated within the body. For example there are multiplicities of other tools like central venous catheter kits with associated sharps, cavity drainage catheter kits, and neonatal lancets, as well as procedures like insulin administration and percutaneous glucose testing, to name a few, where embodiments disclosed herein comprising sonically or ultrasonically driven sharps members may be used to precisely pierce or puncture tissues. Accordingly, the spirit and scope of the present invention is to be construed broadly and limited only by the appended claims, and not by the foregoing specification.

The invention claimed is:

1. A device, comprising:
   a Langevin transducer comprising a first central hollow channel, the first central hollow channel axially extending throughout the first central hollow channel's length, wherein the Langevin transducer has a handle that extends along an entire axial length of a piezoelectric ring and is located in a radial direction outward from the piezoelectric ring so as to cover the piezoelectric ring along the entire axial length of the piezoelectric ring; and
   a sharps member comprising a second central hollow channel, the second central hollow channel axially extending through at least a portion of the second central hollow channel's length, coupled to said Langevin transducer, such that said Langevin transducer and said sharps member share a common fluidic pathway formed by said first and second central hollow channels to allow for the passage of at least one of: bodily tissues, bodily fluids, saline, and medicines; and
   a catheter disposed first through the first central hollow channel so as to be disposed within the piezoelectric ring and the handle that extends in the axial direction along the entire axial length of the piezoelectric ring that is radially outward from the entire piezoelectric ring, wherein the catheter is subsequently disposed through the second central hollow channel and out of the sharps member.

* * * * *